United States Patent
Rwei (10) Patent No.: US 11,883,265 B2
(45) Date of Patent: Jan. 30, 2024

(54) PORTABLE THERMOSHAPABLE FABRIC COMPOSITE HEATING DEVICE KIT

(71) Applicant: NATIONAL TAIPEI UNIVERSITY OF TECHNOLOGY, Taipei (TW)

(72) Inventor: Syang-Peng Rwei, Taoyuan (TW)

(73) Assignee: National Taipei University of Technology, Taipei (TW)

( * ) Notice: Subject to any disclaimer, the term of this patent is extended or adjusted under 35 U.S.C. 154(b) by 395 days.

(21) Appl. No.: 17/235,076

(22) Filed: Apr. 20, 2021

(65) Prior Publication Data

US 2022/0054320 A1 Feb. 24, 2022

(30) Foreign Application Priority Data

Aug. 19, 2020 (TW) .................................. 109128258

(51) Int. Cl.
*A61F 13/04* (2006.01)
*F24H 1/00* (2022.01)
(Continued)

(52) U.S. Cl.
CPC ............ *A61F 13/041* (2013.01); *B29C 35/02* (2013.01); *F24H 1/0072* (2013.01); *F24H 1/06* (2013.01); *A61F 2013/00625* (2013.01)

(58) Field of Classification Search
CPC ........ H05B 3/28; H05B 3/342; A47C 21/048; A61F 2013/00625; A61F 13/041;
(Continued)

(56) References Cited

U.S. PATENT DOCUMENTS 4,411,262 A 10/1983 Von Bonin et al.
4,800,872 A 1/1989 Buese et al.

FOREIGN PATENT DOCUMENTS

EP 1685953 A1 8/2006
TW 363397 U 7/1999
(Continued)

*Primary Examiner* — Ophelia A Hawthorne
(74) *Attorney, Agent, or Firm* — Rosenberg, Klein & Lee (57) ABSTRACT

A portable thermoshapable fabric composite heating device kit mainly comprises a portable heating device and a thermoshapable fabric composite; wherein the portable heating device includes a first box body and a second box body disposed above or inside the first box body. A heating space formed between the bottoms of the two box body bodies is used to accommodate a heating pack. The thermoshapable fabric composite can be accommodated within a receiving space of the second box body. After water is added into the first box body to flood the heating pack, and a lid is placed to cover the top, the heat-generating material in the heating pack contacts the water to generate water vapor during an exothermic reaction. The water vapor enters the receiving space, in which the thermoshapable fabric composite is stored, through the multiple pores at the bottom of the second box body. The generated thermal energy will heat the thermoshapable fabric composite without the need for open flame or electricity. That is, the thermoshapable fabric composite can be heated and softened, so that the thermoshapable fabric composite can be used in the field without reliance on external elements, such as conventional heating or electricity, in order to achieve the purpose of providing first aid such as bandaging and fixation, and to prevent secondary injuries.

12 Claims, 5 Drawing Sheets

(51) Int. Cl.
    *A61F 13/00*     (2006.01)
    *B29C 35/02*     (2006.01)
    *F24H 1/06*     (2022.01)

(58) Field of Classification Search
    CPC . A61F 13/04; A61L 15/42; F24H 1/06; F24H 1/0072; B29C 35/02
    See application file for complete search history.

(56) References Cited

FOREIGN PATENT DOCUMENTS

| | | | |
|---|---|---|---|
| TW | M363285 U | 8/2009 | |
| TW | M496439 U | 3/2015 | |
| TW | 201733873 A | 10/2017 | |
| TW | I646982 B | 1/2019 | |
| TW | I648160 B | 1/2019 | |
| TW | M577021 U | 4/2019 | |
| WO | WO-2005103637 A2 * | 11/2005 | ........... A47C 21/048 |

* cited by examiner

PORTABLE THERMOSHAPABLE FABRIC COMPOSITE HEATING DEVICE KIT

BACKGROUND OF THE INVENTION

The present invention relates to a portable thermoshapable fabric composite heating device kit, and more specifically, to a portable heating device kit capable of generating heat without reliance on external elements such as open flame or electricity for shaping a thermoshapable fabric composite.

Gypsum is a sulfate mineral composed of calcium sulfate dihydrate ($CaSO_4 \cdot 2H_2O$) and the main chemical composition is calcium sulfate ($CaSO_4$). Gypsum can be calcined and ground to obtain j-type hemihydrate gypsum ($CaSO_4 \cdot \frac{1}{2}H_2O$), commonly known as "building gypsum", also known as "plaster" or "plaster of Paris". Plaster of Paris casting materials used in medical care in the early days are heavy and thick, and lack the required softness and comfort. Recently, bandages made of plaster of Paris powder (or plaster of Paris bandages) have been widely used in medical limb fixation, such as a temporary medical treatment in emergency rooms for temporary fixation of fractures, dislocations, and the like before further treatment is taken. Alternatively, it can be used directly for limb fixations after operations of fractures and dislocations.

Another type of material that is commonly used to provide fixation, support, and protection, as well as to prevent and correct deformities, is a casting material composed mainly of a light synthetic polymer, such as a synthetic or resin casting bandage. This type of casting material using a synthetic polymer as its main composition is lightweight and can be washed as its property is not affected by water. At the same time, it improves the comfort of the person using it and allows him/her to have better limb mobility. Furthermore, since X-rays can penetrate these casting materials mainly composed of synthetic polymers, medical staff can perform subsequent medical inspections such as X-rays without removing the casting materials.

As mentioned before, plaster of Paris used in the early days for fixating fractures or during healing periods after operations is very heavy and bulky, and lacks the required softness and comfort and tends to cause discomfort to the person wearing it. Plaster of Paris typically hardens in about 5 to 10 minutes, but for the plaster to become completely dry, it will take 1 to 2 days. This is quite a long time as patients cannot move freely before the plaster is dried and set. Furthermore, plaster of Paris cannot come into contact with water since water will gradually dissolve and soften the plaster and cause it to crack. In addition, plaster of Paris has poor air permeability and may cause allergies and skin rashes. Typically, in the first week of immobilizing treatment using a plaster cast, the patient's injured area may get swollen and the cast that was already set may feel too tight for the patient, and the patient may experience bad blood circulation and pain. In the second week, when the swelling begins to diminish, the plaster cast may feel too loose, failing to provide the fixation needed. Once the plaster is set, the process of removing and reshaping it can be relatively time consuming and inconvenient. In this situation, it may cause discomfort to patients and prolong the healing periods; in some cases, it might even result in complications such as compartment syndrome.

On the other hand, commercially available resin casting bandages are mainly composed of water-hardenable synthetic polymer casting materials (e.g. reactive polyurethane) that can be hardened and set once they come into contact with water or a solution that includes a catalyst or a curing agent, such as 3M™ Scotchcast™ Rigid Casting Tape, "Constructional Material" disclosed in U.S. Pat. No. 4,411,262, or "Ravel-free Orthopedic Casting Tapes" disclosed in U.S. Pat. No. 4,800,872. When in use, the polymer casting material can be encased around a part of a user that requires orthopedic fixation before immersing it in water or coming into contact with water for a period of time, or alternatively, the casting material can first be immersed in water and then placed around the part of the user that requires orthopedic fixation before it is hardened, and after a period of reaction time, the casting material is hardened to hold the particular part of the user in place. Since the water hardenable synthetic polymer casting materials will start to harden as soon as it is in contact with water or moisture and it is an irreversible reaction, so it cannot be reshaped or reused and the casting materials have to be stored properly in sealed devices to prevent them from coming into contact with water or moisture.

High molecular polymer materials with shape memory capability are a type of smart materials that has the ability to recover from a deformed transient state (temporary shape) to its permanent state (original shape) under an external stimulus, such as heat, light, electrical field, magnetic field, etc., and so has been widely used in the electronic circuit elements, thermal sensing elements, biomedical fields. Thermoshapable fabric composite materials, structures, pads, protective equipment and thermoshapable fabric composite bandages containing these type of high molecular polymer materials with shape memory capability have been developed, for example, those disclosed in publications, such as Taiwan Patent Publication No. I646982 entitled "Shape Memory Spacer Fabric Composite", Taiwan Patent Publication No. I648160 entitled "Method for Fabricating a Spacer Fabric Composite, Coating Machine and Composite Fabricated by Method Thereof", Taiwan Utility Model Publication No. M577021 entitled "Cushion Composite Structure, Pad Body and Personal Protective Equipment", Taiwan Patent Application No. 109116737 entitled "Thermoplastic Thin 2D Mesh Composite Structure and Related Products and Method for Producing the Same", and Taiwan Utility Model Application No. 109206227 entitled "Thermoplastic Thin 2D Mesh Composite Structure and Related Products", the entire contents of which are incorporated herein by reference.

In order for the thermoshapable fabric composites (e.g. thermoshapable fabric composite bandages) to soften and become pliable, a heating device that can generate heat is usually required. For example, a heating device, such as a microwave or an oven, is needed to raise the temperature of a thermoshapable fabric composite above the melting temperature (i.e. Tm point) of the high molecular polymer coated thereon. This undoubtedly limits the places where the thermoshapable fabric composites can be used, that is, to places where there is an accessible heat source, such as indoor or some other specific locations, in order to heat the thermoshapable fabric composite. As a result, thermoshapable fabric composites cannot be used as a first and immediate treatment in outdoor first aid stations, medical services in the army, field search and medical services, and the like, if a heat source such as electricity or open flame is not accessible.

SUMMARY OF THE INVENTION

In view of the above shortcomings of the traditional bandages, a portable thermoshapable fabric composite heating device kit without reliance on open flame or electricity is provided. With the heating device of the present invention, the thermoshapable fabric composite (e.g. a thermoshapable fabric composite bandage) does not come into direct contact with a heat source; rather, the thermoshapable fabric composite bandage is heated by water vapor generated by a heat pack coming into contact with water, and the temperature of the bandage is raised above the melting point of the high molecular polymer contained therein, thereby softening the bandage to allow shaping and bandaging.

One objective of the present invention is to provide a portable thermoshapable fabric composite heating device kit that is not constrained by the environment.

Another objective of the present invention is to provide a portable thermoshapable fabric composite heating device kit that can be reshaped and reused while not being constrained by the environment.

In order to achieve the above objectives and technical effects, the technical means employed by the present invention includes: providing a portable thermoshapable fabric composite heating device kit, which may include a portable heating device and a thermoshapable fabric composite. The portable heating device may include: a first box body including a first opening at the top; a second box body inserted into the first box body, or stacked directly on top of the first box body, the second box body having a receiving space and a plurality of pores at the bottom thereof, wherein a heating space is formed between the bottom of the second box body and the bottom of the first box body; a heat pack disposed in said heating space including a bag made of a water permeable material and a heat-generating material contained in the bag, and a lid for concealing the first opening of the first body and/or the second opening of the second body inserted in the first body.

The thermoshapable fabric composite above can be accommodated in the receiving space of the second box body. By means of a heating method, a high molecular polymer with shape memory capability can be coated onto a fabric to form the thermoshapable fabric composite. The fabric used by the thermoshapable fabric composite containing the high molecular polymer with shape memory capability can be a three-dimensional (3D) fabric or two-dimensional (2D) fabric.

The high molecular polymer with shape memory capability of the present invention is in a solid state under normal temperature, and begins to soften as temperature increases. The melting point (Tm point) of the high molecular polymer is greater than about 65° C.~70° C. Therefore, using the portable heating device of the present invention, the temperature of the polymer can be raised higher than the Tm point, such that the thermoshapable fabric composite can be completely softened and can be manipulated and shaped by a user for bandaging and fixation.

According to the present invention, after water is added into the first box body to flood the heating pack, the second box body containing the thermoshapable fabric composite is inserted into the first box body (or stacked on top of the first box body in accordance with other embodiments) and a lid is placed to cover the top, the heat-generating material in the heating pack contacts the water to generate water vapor during an exothermic reaction. The water vapor enters the receiving space of the second box body via the pores and thermal energy is conducted to the thermoshapable fabric composite contained in the receiving space. The generated thermal energy will heat the thermoshapable fabric composite without the need for open flame or electricity. That is, the thermoshapable fabric composite can be heated and softened, so that the thermoshapable fabric composite can be used in the field without reliance on external elements.

In the portable heating device above, the lid can be further provided with at least one vent for discharging excess water vapor, preventing the temperature in the boxes to become too high, while reducing pressure and improving vapor convection in the boxes, so as to achieve fast softening and improved safety. In some embodiments, a plurality of ribs may be further disposed inside the first box body for supporting the second box body inserted in the first box body.

According to the present invention, the water permeable material of the heat pack may include cloth or paper. The heat-generating material in the heat pack may include calcium oxide (CaO, or so called quicklime) granules or powder. The first box body, the second box body, and the lid can be made of a material including silicone, paper, plastic, etc.

The above and other objectives, technical effects and features of the present invention can be more fully understood from the detailed descriptions given below with reference to the attached drawings.

DETAILED DESCRIPTION

The following descriptions and illustrations of the present invention are provided to facilitate understanding of the features, such as the structures, functions and effects, and technical contents of the present invention. It can be appreciated that the various features depicted in the drawings are not drawn to scale and are for illustrative purpose only. Components that are the same or similar in drawings illustrating different embodiments of the present invention are denoted with the same reference numbers, and such similarities and repetitions are used to concisely describe the present invention and it is not necessarily imply any particular relationships between the different embodiments and/or structures recited. In addition, terms used in the specification for describing spatial relationships, such as "upper/lower", and the like, are merely used to facilitate the descriptions of relative relationships between one or more element(s) or feature(s) or with another (or some other) element(s) or feature(s) in the drawings. These spatial terms are not to be construed as limiting the one or more element(s) or feature(s) to a particular spatial location with respect to the another (or some other) element(s) or feature(s), but rather encompassing different directions of the element(s) or feature(s). It should be noted that the appended drawings are provided for reference and illustration only, and should not be construed as a limitation of the present invention in any way.

The terms "about", "approximately", "substantially" used in this specification usually represent within 20%, preferably within 10%, more preferably within 5%, or within 3%, or within 2%, or within 1%, or within 0.5% of a given numerical value or range. The given numerical value is an approximate value, in other words, without specific explanations, the meaning of "about", "approximately" or "substantially" is implied.

Figure 1:
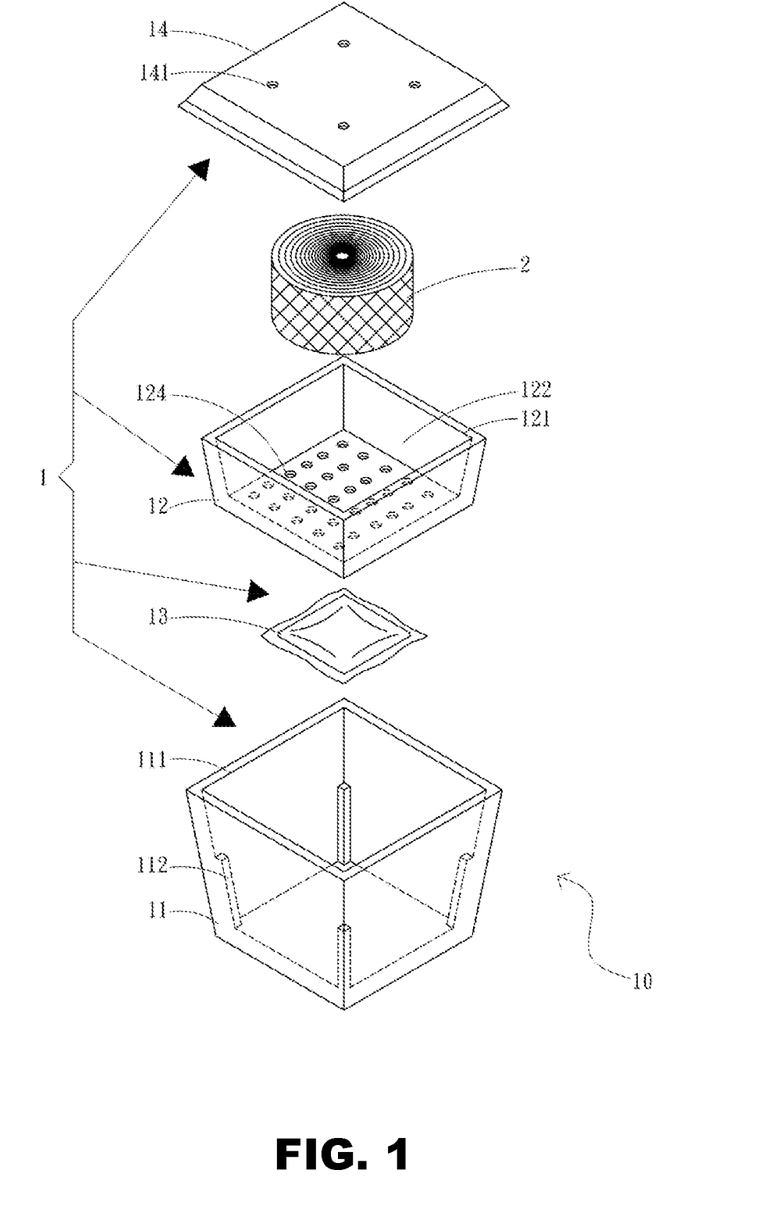
FIG. 1 is a perspective view of a preferred embodiment of the present invention.

Referring to FIG. 1, a portable thermoshapable fabric composite heating device kit 10 includes a portable heating device 1 and a thermoshapable fabric composite 2. The portable heating device 1 includes a first box body 11, a second box body 12, a heat pack 13 and a lid 14. A first opening 111 is formed at the top of the first box body 11, and in some embodiments, a plurality of ribs 112 are provided within the first box body 11. As an example, referring to FIG. 1, a rib 112 is formed at each of the four corners of the first box body 11 for supporting the second box body 12.

Figure 2:
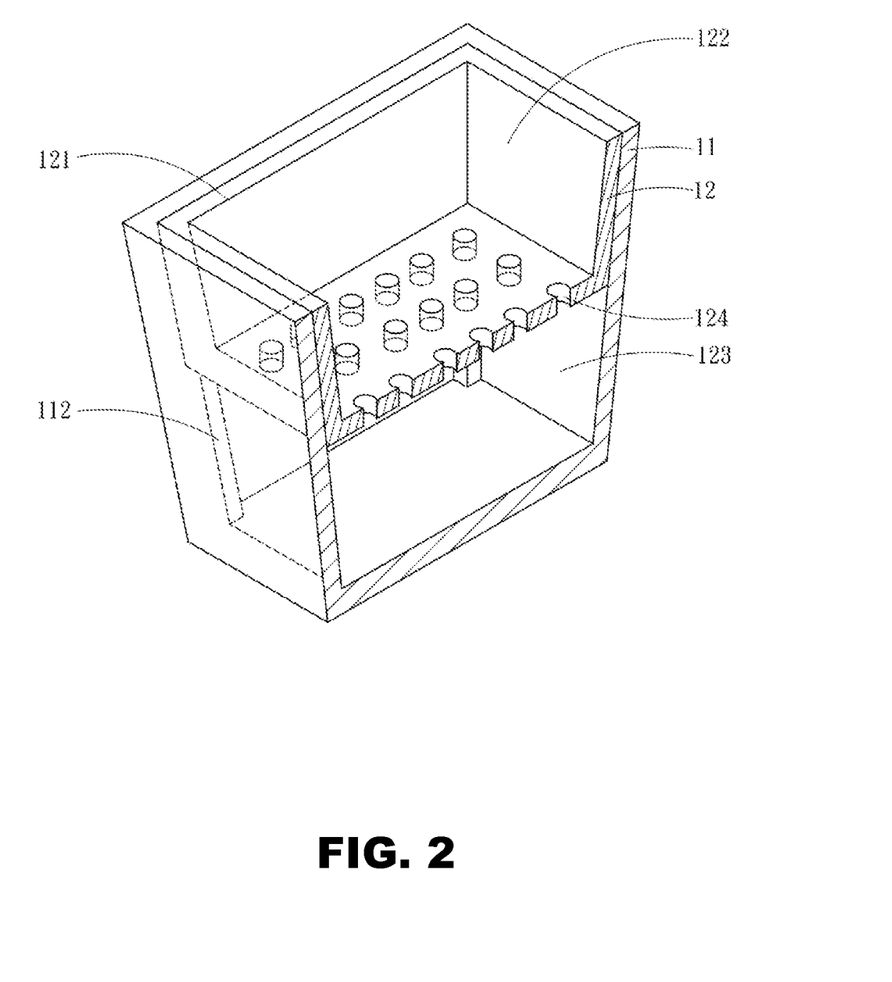
FIG. 2 is a first cross sectional view of a partial assembly of components in accordance with a preferred embodiment of the present invention.

A receiving space 122 is formed within the second box body 12, and a second opening 121 is formed at the top of the second box body 12. There are a plurality of pores 124 formed at the bottom of the second box body 12 for allowing water vapor to flow through. A heating space 123 is formed between the bottom of the second box body 12 and the bottom of the first box body 11 for accommodating the heat pack 13. The second box body 12 can be inserted into the first box body 11, or stacked directly on top of the first box body 11 (not shown). When the second box body 12 is inserted into the first box body 11, the second opening 121 of the second box body 12 can protrude above the first opening 111 of the first box body 11 (not shown). Alternatively, the second opening 121 of the second box body 12 can be flush with (i.e. at the same level as) the first opening 111 of the first box body 11. When the second box body 12 is stacked on top of the first box body 11, the bottom of the second box body 12 conceals the first opening 111 of the first box body 11. In some embodiments, as can be seen in FIG. 2, the second box body 12 is inserted in the first box body 11 and supported by the plurality of ribs 112 in the first box body 11, wherein the second opening 121 of the second box body 12 is positioned on the same level as the first opening 111 of the first box body 11.

Figure 5:
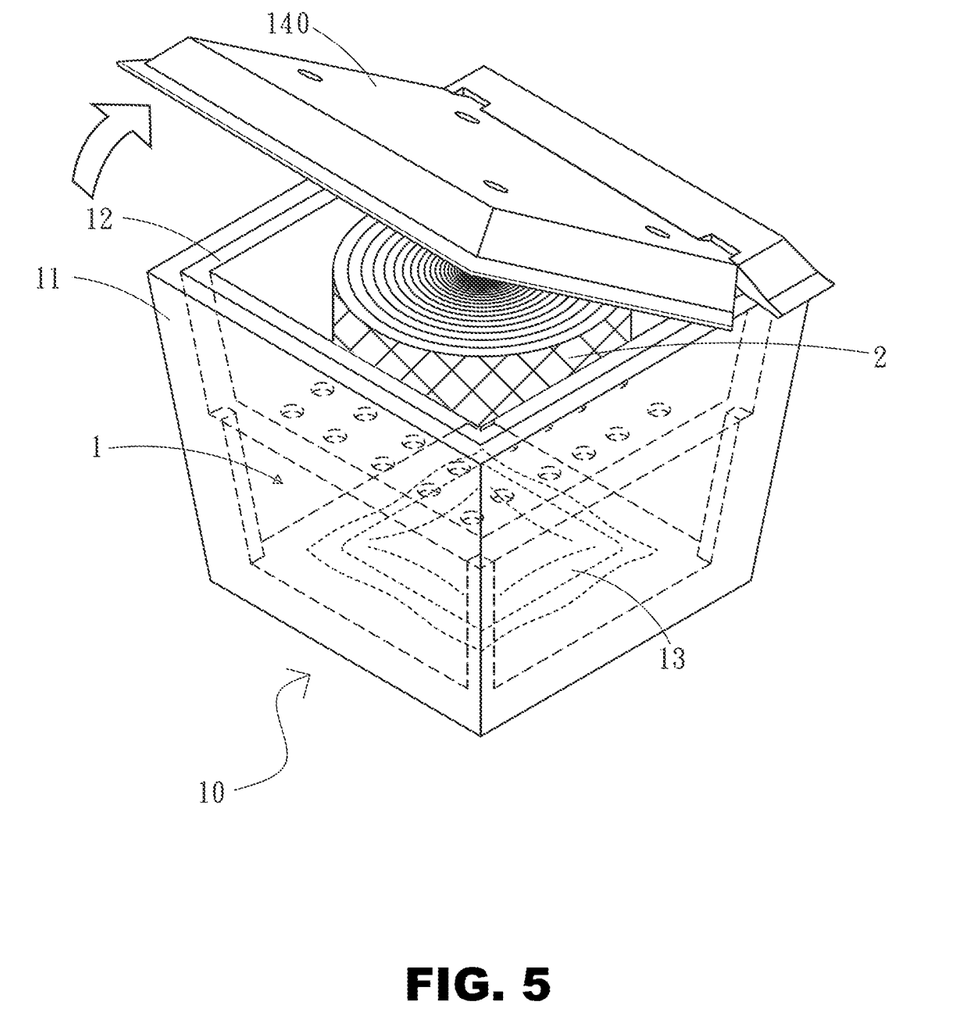
FIG. 5 is a perspective view of an embodiment of the present invention with a flip-top lid.

The lid 14 can be detachable as shown in FIG. 1, which can be used to cover the first opening 111 of the first box body 11 and/or the second opening 121 of the second box body 12. One or more vents 141 can be further provided in the lid 14 for discharging excess water vapor and preventing the temperature becoming too high, and at the same time, reducing the pressure and steam convection to achieve the purposes of increased softening and improved safety. A plurality of vents 141 are shown in FIG. 1. Alternately, as shown in FIG. 5, a lid 140 can be attached to one side of the first box body 11 or the second box body 12 as a flip-top lid.

Figure 3:
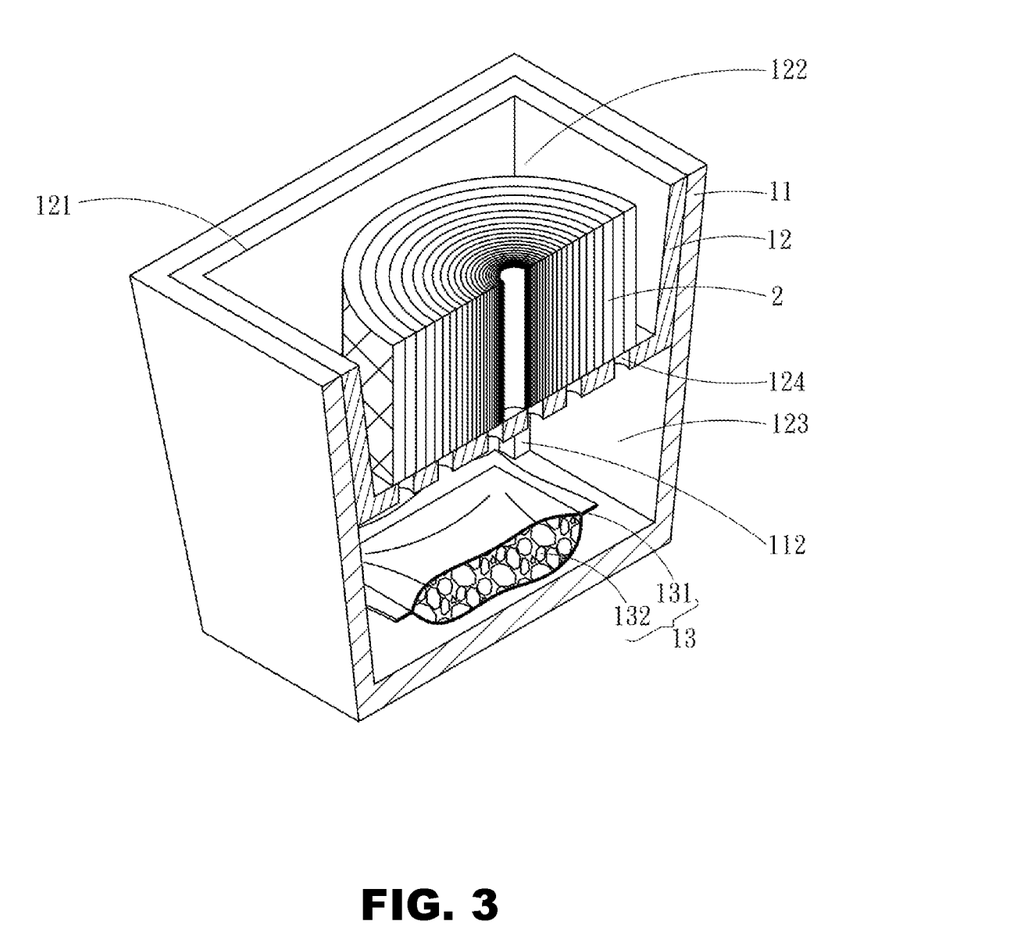
FIG. 3 is a second cross sectional view of a partial assembly of components in accordance with a preferred embodiment of the present invention.
Figure 4:
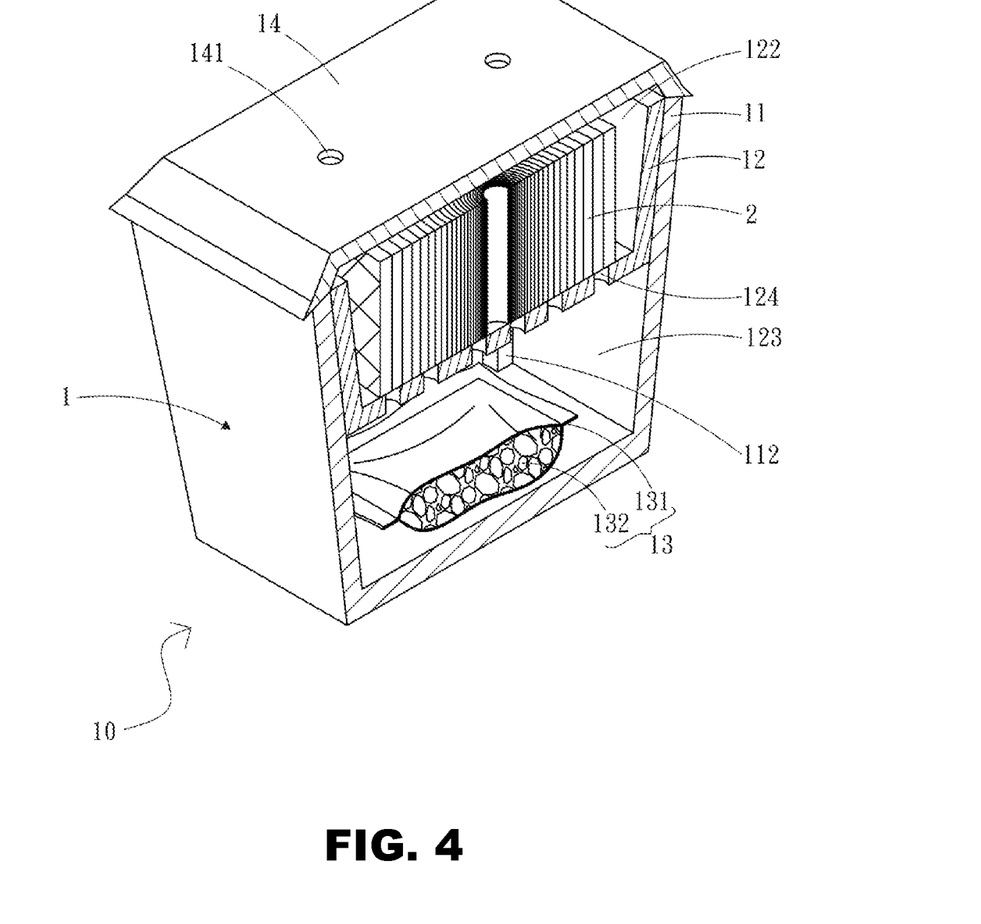
FIG. 4 is a third cross sectional view of the assembly of components in accordance with a preferred embodiment of the present invention.

Referring to FIGS. 3 and 4, the heat pack 13 can be placed in the heating space 123 formed between the first box body 11 and the second box body 12. The heat pack 13 includes a bag 131 made of a water permeable material (e.g. paper or cloth) and a heating generating material 132 contained in the bag 131. The heating generating material 132 can be calcium oxide granules or powder. For easy portability and reuse, the first box body 11, the second box body 12, and the lid 14 can be made of materials such as silicone, paper, or plastics.

The thermoshapable fabric composite 2 of the present invention can be accommodated in the receiving space 122 of the second box body 12 described above. A high molecular polymer with shape memory capability can be coated on a fabric by means of a heating method to form the thermoshapable fabric composite 2. The fabric body used in the thermoshapable fabric composite 2 containing a high molecular polymer with shape memory capability can be a three-dimensional (3D) fabric, which is mainly formed by yarns of different heights in the Z-axis direction between the upper and lower surface layers (i.e., X and Y planes) and perpendicular to the X and Y planes to form 3D spacers, which offers mechanical support, or alternatively, a two-dimensional (2D) fabric, in which no spacer is present between the lower and upper surface layers forming the X and Y planes. A thermoshapable thin 2D mesh is an example of the 2D fabric.

The melting point (Tm point) of the high molecular polymer with shape memory capability is greater than about 65° C.~70° C. Using the portable heating device 1 of the present invention, the temperature of the polymer can be raised higher than the Tm point, such that the thermoshapable fabric composite 2 containing the high molecular polymer can be manipulated and shaped by a user for encasing and fixating a subject. The high molecular polymer with shape memory capability can be selected from the group consisting of at least one random copolymer or block copolymer of polyester, polyurethane (PU), polyamide, polyol, and polycaprolactone (PCL).

In addition, in some embodiments, the high molecular polymer with shape memory capability used by the present invention can be formed without blending, such that the high molecular polymer after heating (e.g. above the Tm point) once and cooling will still have chain-entangled structures, which would otherwise be lost if a blending treatment is used due to interference by the low molecular weight compounds contained therein, which in turn would render the loss of the Tm point and the lowering of its mechanical strength. The high molecular polymer of the present invention can be formed by a heating method, such that after heating (e.g. above the Tm point) and cooling, the high molecular polymer will still have chain-entangled structures, so it maintains its structure and the Tm point. As such, the thermoshapable fabric composite 2 of the present invention can be repetitively heated to deformation, allowing it to be reshaped and reused multiple times.

According to the present invention, when a user wishes to use the thermoshapable fabric composite 2 for fixation, the first box body 11 can first be filled with water to an appropriate level, such that the heat pack 13 disposed therein is flooded. Then, the second box body 12 containing the thermoshapable fabric composite 2 is positioned above (not shown) or inside the first box body 11. As shown in FIG. 2, in some embodiments, the second box body 12 is inserted into the first box body 11, such that it is seated on top of the plurality of ribs 112. Thereafter, the lid 14 is placed to cover the top. Once the heat-generating material in the heat pack 13 is in contact with water, considerable quantity of water vapor with thermal energy is generated during an exothermic reaction. The water vapor passes through the plurality of pores 124 at the bottom of the second box body 12 and enters into the receiving space 122 of the second box body 12, and thermal energy is then conducted to the thermoshapable fabric composite 2 disposed inside the receiving space 122. The generated thermal energy will heat the thermoshapable fabric composite without the need for open flame or electricity. That is, the thermoshapable fabric composite 2 can be heated and softened, so that the thermoshapable fabric composite can be shaped and used without reliance on external elements.

In a preferred embodiment, the heating generating material 132 included in the heat pack 13 can be calcium oxide, or commonly known as quicklime. Calcium oxide contacts with water and then undergoes an exothermic reaction, producing calcium hydroxide ($Ca(OH)_2$) and a large amount of water vapor with thermal energy. The water vapor enters the receiving space 122 through the pores 124 at the bottom of the second box body 12, and conducts thermal energy to the thermoplastic fabric composite 2. As the temperature rises to a certain degree, for example, higher than the Tm point of the coated polymer (e.g. 65° C.~70° C.), the thermoplastic fabric composite 2 begins to soften. After a moderate heating time, the thermoplastic fabric composite 2 is completely softened, and then the thermoplastic fabric composite 2 can be taken out and used. For example, it can be used for temporary bandaging and fixation in outdoor courts for fractures, dislocations, etc., and can prevent secondary injuries. With the present invention, the thermoplastic fabric composite material 2 can be heated and softened without open flame and electricity, and the thermoplastic fabric composite 2 can be used for first aid treatment such as bandaging and fixation without being restricted by the environment. The calcium hydroxide produced after the exothermic reaction of calcium oxide (quicklime) with water is a substance found in natural soil and can be used for improving soil structure and reducing acidity of the soil, so it will not cause pollution or harm to the environment.

EXAMPLES

According to the present invention, samples of thermoshapable fabric composite bandages provided by TSM Smart Materials Co., Ltd. having a width of about 5 cm, length of about 180 cm, and thickness of 0.1 cm weighing approximately 72 g per roll were used for the experiments. A portable heating device that can hold four rolls of thermoplastic fabric composite bandages was used to heat and soften the bandage samples. For example, the size of the first box body of the heating device was about 17.4 cm in length and about 17.4 cm in width and about 8.05 cm in height. The size of the second box body was about 15.8 cm in length and 15.8 cm in width and 5.5 cm in height, and the size of the lid was about 17.8 cm in length and 17.8 cm in width. The experimental results are shown in Table 1.

TABLE 1

| No. | Quicklime (g) | Water (g) | Heating Time (min) | Harden Cooling Time (min) | Result |
|---|---|---|---|---|---|
| 1 | 90 | 300 | 8 | 2.5 | Sample soft and sticky, but sample temperature too high |
| 2 | 70 | 300 | 10 | 2.5 | Sample soft and sticky, but sample temperature too high |
| 3 | 50 | 300 | 8 | 2 | Sample fully softened and sticky, quantity of vapor generated moderate |
| 4 | 40 | 300 | 7.5 | X | Center of sample not fully softened |
| 5 | 30 | 300 | 6.3 | X | Center of sample not fully softened |
| 6 | 20 | 300 | 6 | X | Only small part of outer layer of sample softened |

As can be seen from the experiments above, the water vapor generated from reaction of 50 g of calcium oxide (quicklime) with 300 g of water for 8 minutes was enough to fully soften the four rolls of thermoshapable fabric composite bandages and allow them to have certain stickiness. The time it took for the bandages to harden was around 2 minutes. This would give a user enough time to shape the bandage around a part to be treated. When the content of quicklime was more than 70 g, the temperatures of the heated samples became too high for the skin.

A portable heating device having the capacity of holding just one roll of thermoplastic fabric composite bandage was used to heat and soften the bandage samples. For example, the size of the first box body of the heating device was about 9.5 cm in length and about 9.5 cm in width and about 11.2 cm in height. The size of the second box body was about 9.5 cm in length and 9.5 cm in width and 8.4 cm in height, and the size of the lid was about 9.5 cm in length and 9.5 cm in width. The experimental results are shown in Table 2.

TABLE 2

| No. | Quicklime (g) | Water (g) | Heating Time (min) | Harden Cooling Time (min) | Result |
|---|---|---|---|---|---|
| 1 | 25 | 90 | 10 | X | Too much quicklime, so sample polluted by quicklime and water, and not sticky |
| 2 | 20 | 90 | 9 | 2 | Sample soft and sticky, but sample temperature too high |
| 3 | 15 | 90 | 8 | 2.6 | Sample fully softened and sticky, quantity of vapor generated moderate |
| 4 | 10 | 90 | 6 | 1 | Center of sample not fully softened |
| 5 | 5 | 90 | 5 | X | Only small part of outer layer of sample softened |

As can be seen from the experiments above, the water vapor generated from reaction of 15 g of quicklime with 90 g of water for 8 minutes was enough to fully soften the roll of thermoshapable fabric composite bandage and allow it to have a certain stickiness. The time it took for the bandage to harden was also around 2 minutes. This would give the user enough time to shape the bandage around a part to be treated.

15 g of quicklime and water at different ratios were put together to undergo exothermic reactions and generate enough water vapor to soften one roll of thermoshapable fabric composite bandage sample (about 72 g). The experimental results are shown in Table 3.

TABLE 3

| Quicklime:Water | Quicklime (g) | Water (g) | Heating Time (min) | Hardening Cooling Time (min) | Result |
|---|---|---|---|---|---|
| 1:2 | 15 | 30 | 8 | X | Center of sample not fully softened |
| 1:3 | 15 | 45 | 8 | 2.3 | Sample soft and sticky, no water residue |
| 1:4 | 15 | 60 | 8 | 2.4 | Sample soft and sticky, no water residue |
| 1:5 | 15 | 75 | 8 | 2.5 | Sample soft and sticky, small amount of water residue |

TABLE 3-continued

| Quick-lime: Water | Quick-lime (g) | Water (g) | Heating Time (min) | Hardening Cooling Time (min) | Result |
|---|---|---|---|---|---|
| 1:6 | 15 | 90 | 8 | 2.6 | Sample fully softened and sticky, substantial amount of water residue |
| 1:7 | 15 | 105 | 8 | X | Too much water vapor and water, so sample rendered unusable as part of it was polluted by quicklime and water |

As can be seen from the experiments above, exothermic reactions of quicklime and water with ratios from 1:3 to 1:6 for 8 minutes were all capable of fully softening the bandage samples contained in the device. The times it took for the bandages to harden were around 2~3 minutes. This would allow enough time for a user to wrap the bandage around a part to be treated. When the ratio of quicklime to water was too low, i.e. less than 1:6 (too much water added), the temperature of the bandage sample was too high as there was too much water vapor, and the bandage was too hot to handle by hand. In addition, there was too much calcium hydroxide solution left in the first box body, making cleaning up more difficult. On the other hand, if the ratio was too high, i.e. greater than 1:3 (too little water added), then there was not enough water vapor generated to soften the bandage, making bandaging more difficult.

Based on the experimental results shown above, in a portable heating device with an appropriate size that matches the number of bandage sample rolls contained, the ratio of quicklime to bandage sample (quicklime/bandage sample) needs to be about 50 g/288 g (that is, the weight of four rolls of bandage samples in Table 1) or about 15 g/72 g (that is, the weight of one roll of bandage sample in Table 2) or more, such that there will be enough quicklime content to generate the vapor heat needed to soften the bandage sample(s) contained in the heating device. Moreover, results in Table 3 show that if the ratio of quicklime to bandage is fixed at 15 g/72 g; the ratio of quicklime to water is from 1:3 to 1:6; and the exothermic reaction lasts for about 8 minutes, then the bandage sample contained in the device can be completely softened. The hardening cooling time of the bandage sample is about 2.6 min (nearly 3 min), which will give the user enough time to wrap the thermoshapable fabric composite bandage around the desired part. Moreover, when the ratio of quicklime to water is too low, that is, less than 1:6 (excess water added), too much water vapor will be generated, and the bandage will be too hot to be handled by hand, and there will also be too much calcium hydroxide solution left in the first box body, making cleaning up afterwards more difficult. On the contrary, if the ratio of quicklime to water is too high, i.e. greater than 1:3 (too little water added), then there will not be enough water vapor generated to soften the bandage, making bandaging more difficult.

While the present subject matters and advantages have been described in detail with respect to specific example embodiments thereof, it will be appreciated that those skilled in the art, upon attaining an understanding of the foregoing can readily produce alternations to, variation of, and equivalents to such embodiments without departing from the spirit and scope of the present disclosure. For example, and without limitation, any individual element(s) of the described invention may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Further, the specific embodiments disclosed in the present invention include a plurality of features that may, in concert or cooperatively, provide a collection of benefits. The present invention is not limited to only those embodiments that include all of these features or that provide all of the stated benefits, except to the extent otherwise expressly set forth in the issued claims. Furthermore, any reference to claim elements in the singular, for example, using the articles "a", "an", "the" or "said", is not be construed as limiting the element to the singular. Accordingly, the scope of the present disclosure is by way of example rather than by way of limitation, and the subject disclosure does not preclude inclusion of such modifications, variations and/or additions to the present subject matter as would be readily apparent to one of ordinary skill in the art. That is, any equivalent alternations and modifications made according to the claims of the present invention are within the purview of the present invention.

What is claimed is:

1. A portable thermoshapable fabric composite heating device kit, comprising at least:
 a portable heating device including:
  a first box body including a first opening at the top;
  a second box body inserted into the first box body having a receiving space and a plurality of pores at the bottom thereof, wherein a heating space is formed between the bottom of the second box body and the bottom of the first box body;
  a heat pack disposed in said heating space including a bag made of a water permeable material and a heat-generating material contained in the bag, and
  a lid for concealing the first opening of the first body and/or the second opening of the second body inserted in the first body; and
 a thermoshapable fabric composite accommodated in the receiving space of the second box body, the thermoshapable fabric composite being a composite formed of a three-dimensional (3D) fabric or two-dimensional (2D) fabric coated with a high molecular polymer with shape memory capability.

2. The kit of claim 1, wherein the second box body of the portable heating device is stacked on top of the first box body, and the lid of the portable heating device is used for concealing the second opening of the second box body.

3. The kit of claim 2, wherein the thermoshapable fabric composite is a thermoshapable fabric composite bandage.

4. The kit of claim 1, wherein the thermoshapable fabric composite has reshaping capability.

5. The kit of claim 1, wherein the lid is provided with at least one vent.

6. The kit of claim 1, wherein the lid is completely detachable.

7. The kit of claim 1, wherein the lid is a flip-top lid connected to one side of the first box body or the second box body.

8. The kit of claim 1, wherein the portable heating device further comprises a plurality of ribs disposed inside the first box body for supporting the second box body.

9. The kit of claim 1, wherein the water permeable material of the heat pack is cloth or paper.

10. The kit of claim 1, wherein the heat-generating material is calcium oxide granules or powder.

11. The kit of claim 1, wherein the first box body, the second box body, and the lid is made of a material including silicone, paper, or plastic.

12. The kit of claim 1, wherein the thermoshapable fabric composite is a thermoshapable fabric composite bandage.

\* \* \* \* \*